(12) United States Patent
Estes (10) Patent No.: US 9,983,055 B1
(45) Date of Patent: May 29, 2018

(54) METHOD FOR MEASURING OPTICAL ATTENUATION IN A LIQUID MEDIUM

(71) Applicant: Lee E Estes, Mattapoisett, MA (US)

(72) Inventor: Lee E Estes, Mattapoisett, MA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days. days.

(21) Appl. No.: 15/718,106

(22) Filed: Sep. 28, 2017

Related U.S. Application Data

(62) Division of application No. 15/153,792, filed on May 13, 2016, now Pat. No. 9,816,859.

(51) Int. Cl.
*G01N 21/00* (2006.01)
*G01J 1/44* (2006.01)
*G01J 1/04* (2006.01)
*G01J 1/42* (2006.01)

(52) U.S. Cl.
CPC ............... *G01J 1/44* (2013.01); *G01J 1/0488* (2013.01); *G01J 2001/4247* (2013.01)

(58) Field of Classification Search
CPC ............... G01N 21/8507; G01N 21/31; G01N 21/0303; G01N 21/59; G01N 21/05
USPC .......................................................... 356/436
See application file for complete search history.

(56) References Cited

U.S. PATENT DOCUMENTS

| | | | | |
|---|---|---|---|---|
| 4,365,896 A | * | 12/1982 | Mihalow | G01J 5/02 356/239.8 |
| 4,986,656 A | * | 1/1991 | Sweeney | G01J 3/44 356/301 |
| 6,449,042 B1 | * | 9/2002 | Hamann | G01N 15/0211 356/339 |
| 2002/0088952 A1 | * | 7/2002 | Rao | G01N 21/9501 250/559.45 |

* cited by examiner

*Primary Examiner* — Md M Rahman
(74) *Attorney, Agent, or Firm* — James M. Kasischke; Michael P. Stanley (57) ABSTRACT

The present invention provides a meter and method of use for measuring an optical attenuation coefficient in a liquid medium. In operation, a collimated beam, produced by a laser of the attenuation meter apparatus, propagates thru the liquid medium with filtered back-scattered light arriving at a camera of the meter. A light image is formed at a focal plane of the camera. The light image is recorded and analyzed by a microcomputer to provide optical beam attenuations coefficients.

5 Claims, 7 Drawing Sheets

METHOD FOR MEASURING OPTICAL ATTENUATION IN A LIQUID MEDIUM

The present application is a divisional application and claims the benefit of U.S. application Ser. No. 15/153,792 filed on May 13, 2016 by the inventor, Lee E. Estes and entitled "Imaging Optical Beam Attenuation Coefficient Meter".

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

(1) Field of the Invention

The present invention is an attenuation meter and method of use for measuring an optical beam in a liquid medium.

(2) Description of the Prior Art

Presently, there are commercially-available meters designed to measure an optical beam attenuation co-efficient "c" in water. The beam attenuation co-efficient equals the natural logarithm of the ratio of the input power to the output power of a single frequency collimated light beam divided by a propagation length. The beam attenuation co-efficient accounts for both absorption and scattering of the light beam.

In order to limit the size of measuring meters; the meters utilize optical propagation paths that are less than one meter in length. In clear water, attenuation lengths (1/attenuation coefficient=1/c) are often greater than eight meters.

The greater, the attenuation length then the greater the effort needed to maintain an acceptable cleanliness on an optical surface. There is also a greater effort needed to maintain the accuracy of measurement electronics and the accuracy of calibration procedures. Because of these real world scenarios, the measurements provided by these meters in clear water are generally non-repeatable and inaccurate to the extent that the measurements are unusable.

As such, there is need for an attenuation meter and method of use that can provide accurate measurements of an optical attenuation coefficient in a liquid medium with comparatively low attenuation rates—such as a clear water environment.

SUMMARY OF THE INVENTION

Accordingly, it is a general purpose and primary object of the present invention to provide a meter for measuring an optical attenuation coefficient in a clear water environment.

It is a further object of the present invention to provide a meter for measuring an optical attenuation coefficient in a liquid medium.

To attain the objects of the present invention, an attenuation meter is provided. In operation, a collimated beam, produced by a laser of the meter, propagates thru water or another liquid medium with filtered back-scattered light arriving at a camera of the meter. A light image is formed at a focal plane of the camera. The light image is then recorded and analyzed by a microcomputer.

To provide measurement accuracy, a maximum water range is chosen to be one half of an expected maximum attenuation length. Also, the laser beam diameter is large enough to maintain beam collimation but not too large so as to minimize the contribution of forward scattering in the measurement.

A major advantage of this invention is making measurements over long propagation paths and providing accurate measurements of optical beam attenuations coefficients in a clear media.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein.

DETAILED DESCRIPTION OF THE INVENTION

Figure 1:
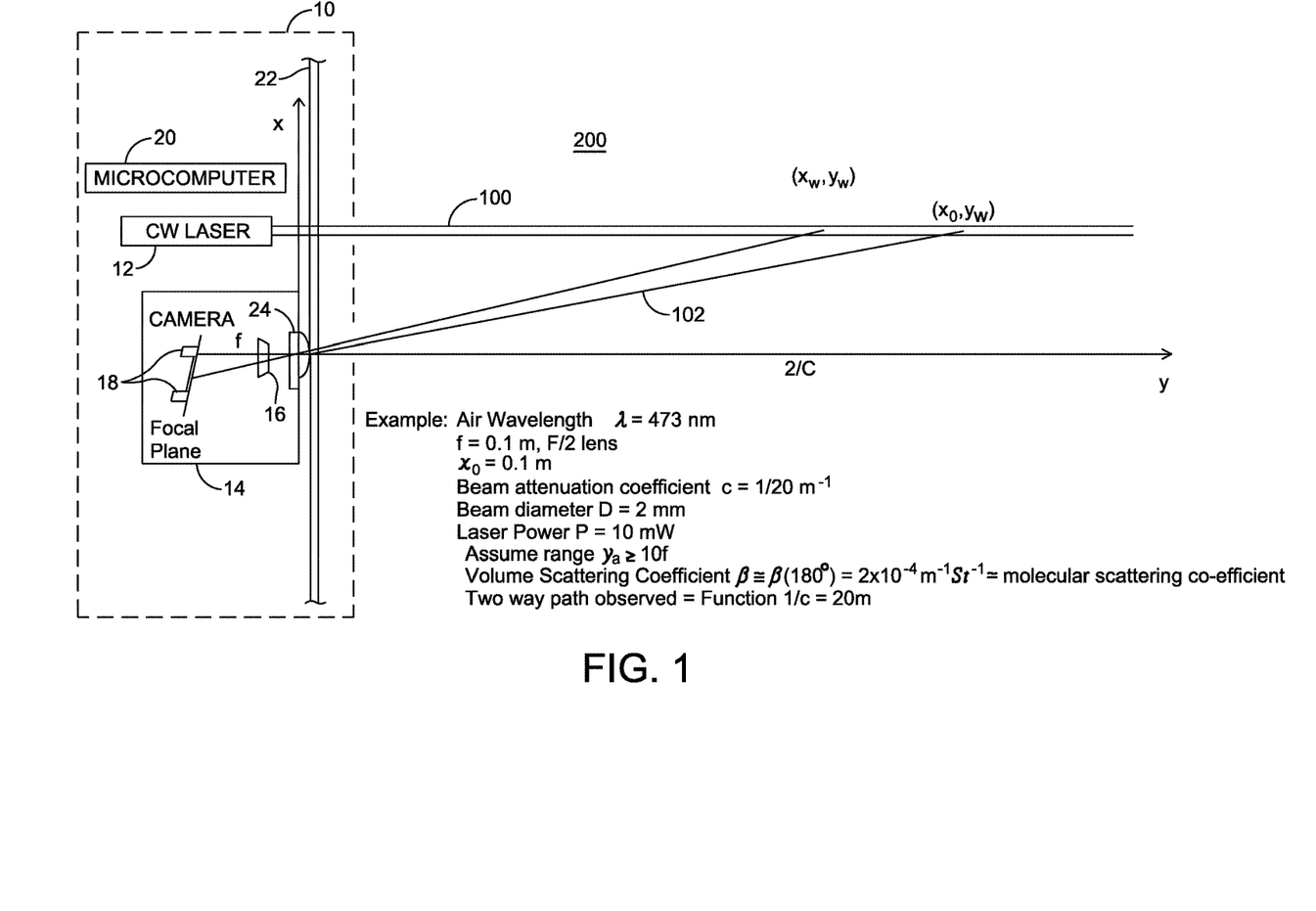
FIG. 1 depicts an operation of an attenuation meter of the present invention in a water environment.

An example of a measurement of a beam attenuation coefficient "c" is depicted in FIG. 1. In the figure, a modeled blue 473 nanometer beam is close to the wavelength of absorption in clear water. Also, a back scattering co-efficient used is approximate to that of natural waters. An assumed maximum range is approximately twelve meters. An attenuation meter 10 and a clear environment such as water 200 to be measured are shown.

The attenuation meter 10 may be used with other liquid mediums. If used with other liquid mediums, the sensed backscattering could be based on density fluctuations in the liquid environment that produce an index of refraction.

In operation, a continuous wave (CW) laser 12 produces a collimated laser beam 100 of a diameter D. As the laser beam 100 propagates thru the water 200, some of the propagated light becomes back-scattered light 102 arriving at the attenuation meter 10. This backscattered light 102 arrives at the meter 10 thru a back scattering of a thermodynamic index of refraction fluctuations and back scattering of particles within the water 200.

A lens 16 of a camera 14 within the attenuation meter 10 uses the backscattered light 102 from the laser beam 100 to form a light image of the laser beam on a tilted focal plane of the camera. Sensors 18 on the focal plane detect the light image. The light image extracts a measurement of the optical beam attenuation coefficient "c" at the wavelength of the laser beam 100. The sensors 18 then transmit data based pixels of the light image to a microcomputer 20. The microcomputer 20 controls the function of the attenuation meter 10 as well as providing analysis of the recorded light image.

An optical window 22 separates the attenuation meter 10 from the water 200 and an optical filter 24 rejects background light by only passing light at the wavelength of the laser beam 100.

Rectangular coordinates (x, y), shown in FIG. 1, are used for selection of parameters. The conditions and definitions entitled "Example" on FIG. 1 are modeled and the results are presented in FIGS. 2-7. To provide adequate measurement accuracy, a maximum water range is chosen to be one half of an expected maximum attenuation length 1/c. The expected maximum attenuation length would be obtained from published data of environmental characteristics.

Also, the beam diameter "D" should be large enough to maintain beam collimation over 1/(2c) but not larger than ½ (1/c) in order to minimize the contribution of forward scattering that falls within the collimated beam in the measurement (i.e. the maximum forward scattering).

A focal length of the lens 16 is chosen so that the image size of a beam at the distance 1/(2c) exceeds the sensor pixel size for realistic pixel (4-20 microns) and focus plane sizes (0.5-2 microns). Using the definitions in FIG. 1, the number of detected electrons within the image per pixel is calculated by Equation (1) with the number of electrons being the signal strength that is recorded.

$$N \cong \frac{QTPt e^{(-2cy_w)} \beta(180°) AA_{pix}(y_a - f)^2}{E_{photon} n^2 f^2 D(x_0^2 + f^2)^{0.5}(x_0^2 + y_a^2)^{0.5}} \quad (1)$$

where "P" is the laser power; "Q" is the sensor quantum efficiency; "T" is the system transmission co-efficient, "n" is the water index of refraction; "A" is the entrance pupil area; $A_{pix}$ is the area of a pixel; "$E_{photon}$" is the energy of a photon; and "f" is the lens focal length.

Figure 2:
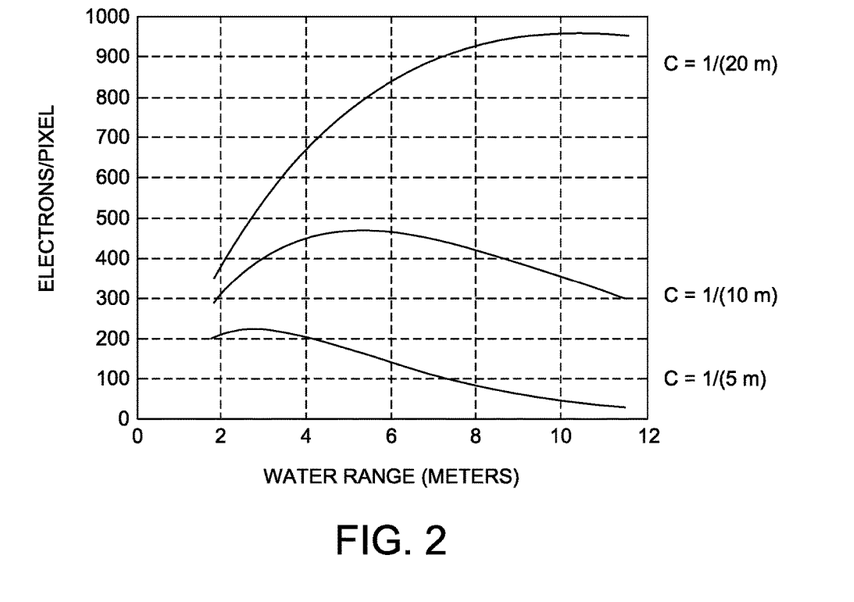
FIG. 2 presents a number of electrons within an image per pixel as a function of water range for an attenuation coefficient of $c=1/(20 \text{ m})$, $c=1/(10 \text{ m})$ and $c=1/(5 \text{ m})$ with the number of pixels produced during the operation of the attenuation meter.

FIG. 2 depicts the number of electrons "N" as a function of water range for an attenuation coefficient of c=1/(20) meters, c=1/(10) meters, and c=1/(5) meters. The figure clearly shows that the shapes for varying values of beam attenuation are very different. Thus, fitting the shape of experimental results to those predicted by Equation (1) will produce a measurement of the beam attenuation coefficient, c.

Figure 3:
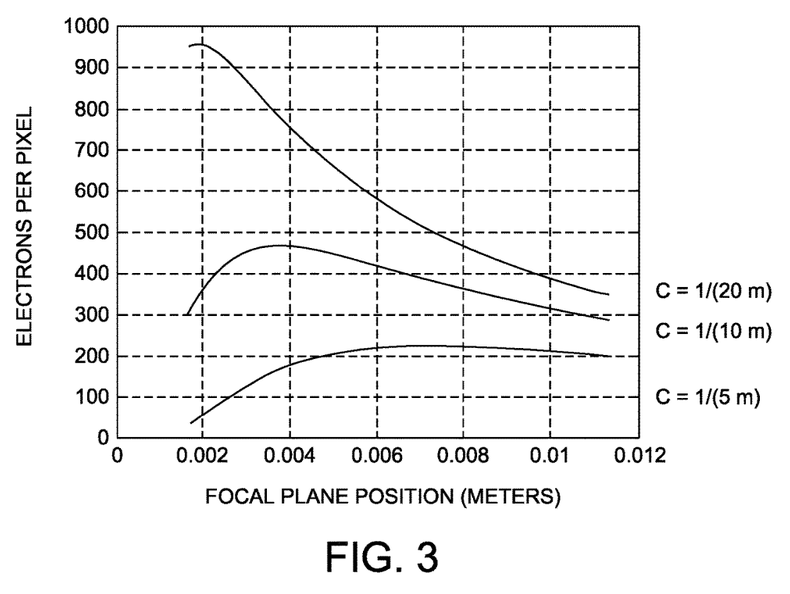
FIG. 3 presents a number of electrons within an image per pixel as a function of a focal plane position for an attenuation coefficient of $c=1/(20 \text{ m})$, $c=1/(10 \text{ m})$ and $c=1/(5 \text{ m})$.
Figure 4:
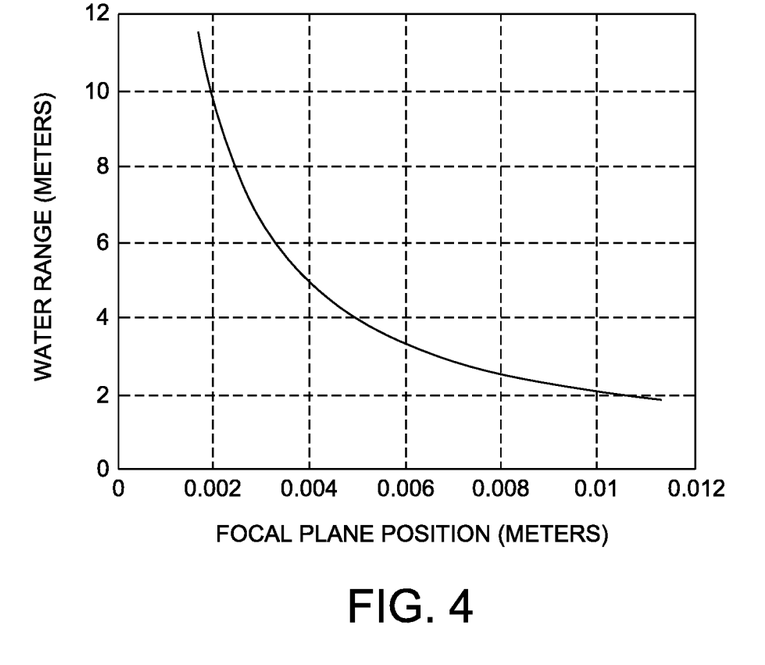
FIG. 4 presents a water range corresponding to a focal plane location.

FIG. 3 presents the same results as a function of focal plane position. FIG. 4 presents the water range, $y_w$, corresponding to focal plane location, S, and f is the focal length given by $$S = \frac{f(x_0^2 + f^2)^{0.5}}{(y_w - f)} \quad (2)$$

Figure 5:
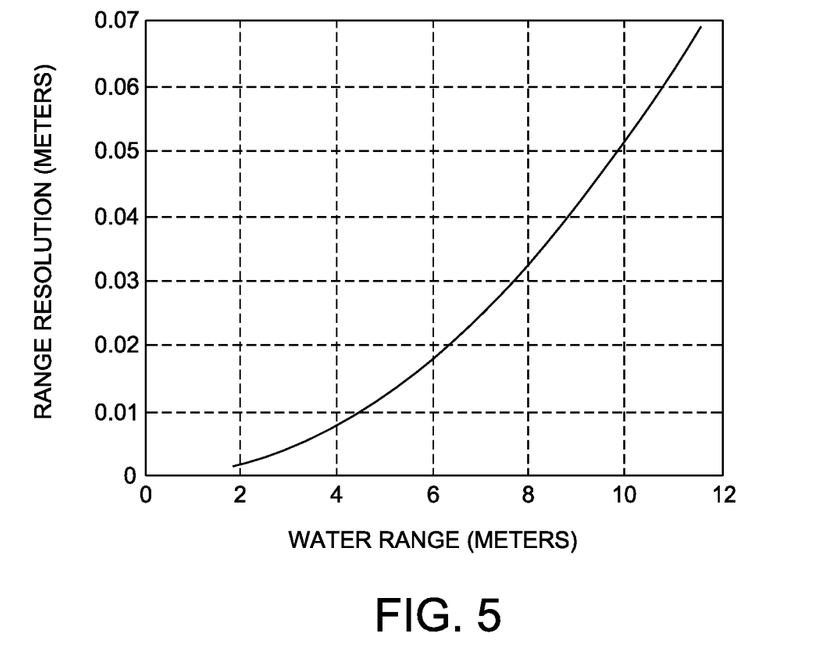
FIG. 5 presents a range resolution defined by a range extent covered by a single pixel along a focal plane as a function of a water range.

FIG. 5 presents the range resolution "r" defined by the range extent covered by a single pixel along the focal plane as a function of water range given by:

$$r = \frac{npix(y_w - f)^2}{f(x_0^2 + f^2)^{0.5}} \quad (3)$$

where "n" is the indexed refraction and "pix" is the pixel size.

Summing over a transverse image extent (beam size perpendicular to the plane of FIG. 1), the total electrons within a range cell is given by $$N_{TOTAL} = \frac{N \, D \, f}{y_w pix} \quad (4)$$

Figure 6:
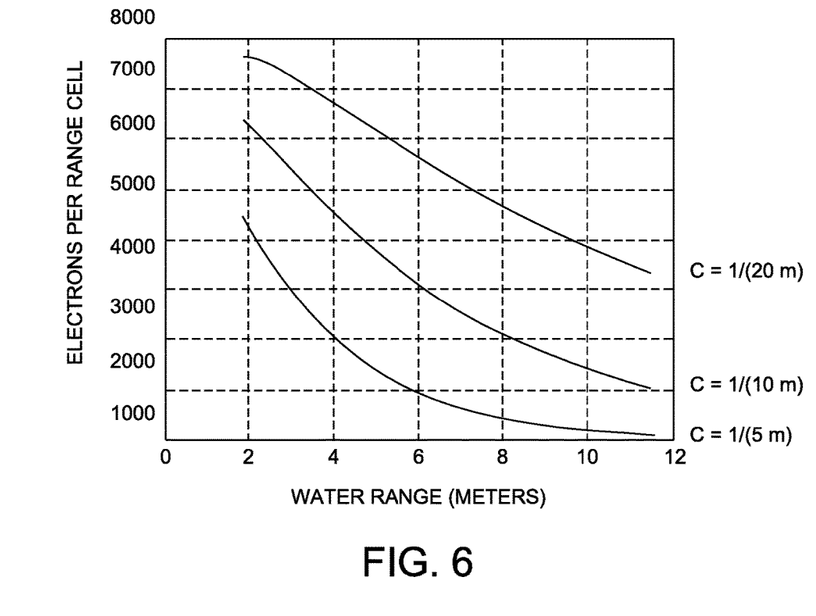
FIG. 6 presents a total of electrons within a range cell given.
Figure 7:
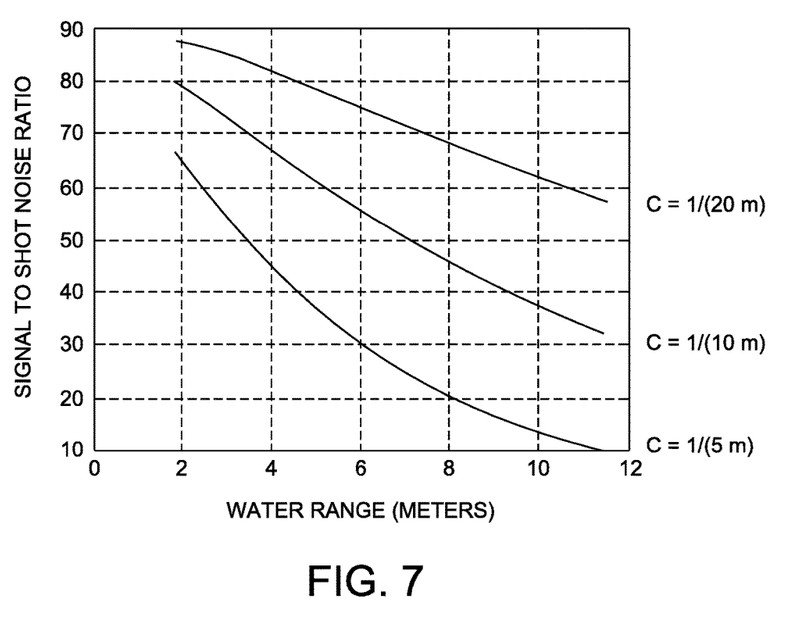
FIG. 7 presents a range cell to shot noise given by Equation (5).

The results of applying Equation (4) are presented in FIG. 6. FIG. 7 presents a "signal-to-shot noise" given by Equation (5).

$$\text{Signal to shot noise} = (N_{TOTAL})^{0.5} \quad (5)$$

An advantage of the present invention is the ability to obtain measurements over long propagation paths and therefore provide accurate measurements of optical beam attenuation coefficients. Another advantage of the invention is that relatively low cost power continuous wave lasers are used rather than short duration pulsed lasers.

The attenuation meter 10 can be deployed as a self-contained module and can be powered by batteries. Furthermore, the attenuation meter 10 can be deployed on vehicles such as unmanned underwater vehicles or deployed from a separate platform with an umbilical cable that supplies electrical power and access to stored data and results. The attenuation meter can contain more than one color light source to provide measurements at more than one wavelength.

The foregoing description of the preferred embodiments of the invention has been presented for purposes of illustration and description only. It is not intended to be exhaustive nor to limit the invention to the precise form disclosed; and obviously many modifications and variations are possible in light of the above teaching. Such modifications and variations that may be apparent to a person skilled in the art are intended to be included within the scope of this invention as defined by the accompanying claims.

What is claimed is:

1. A method for measuring optical attenuation in a liquid medium, said method comprising the steps of:
providing an attenuation meter having an optical window with a first and second section with the optical window being an outer section of the attenuation meter and with the optical window separating an interior of the attenuation meter from the liquid medium, a continuous wave laser positioned as a first component within the interior, an optical filter positioned interior to the optical window in the attenuation meter in which the filter passes light at a wavelength of the laser beam from light which passes thru the second section of the optical window, a camera with a focal plane with the camera positioned as a second component within the interior, at least one sensor operationally connected to the focal plane and a microcomputer operationally connected to the sensor;
choosing a maximum water range as half of a maximum attenuation length;
projecting a collimated laser beam from the laser onto the liquid medium;
producing a back-scattered light in the liquid medium with the laser beam;
passing the back-scattered light thru the optical filter;
forming a light image of the backscattered light passed thru the optical filter;
sensing the light image with the sensor;
transmitting data with the sensor based on the sensed light image;
analyzing the transmitted data with the microcomputer; and determining a beam attenuation coefficient in the liquid medium based on the transmitted data.

2. The method in accordance with claim 1, further comprising the steps of producing a measurable diameter of the laser beam that maintains beam collimation over 1/(2c) where "c" is a beam attenuation coefficient; and achieving a maximum amount of forward scattering by the laser beam.

3. The method in accordance with claim 2, said method further comprising the step of graphing the number of electrons within the light image per pixel as a function of water range for attenuation coefficients based on completion of said analyzing step; and fitting data of said graphing step to results of $$N \cong \frac{QTPte^{(-2cy_w)}\beta(180°)AA_{pix}(y_a - f)^2}{E_{photon}n^2 f^2 D(x_0^2 + f^2)^{0.5}(x_0^2 + y_a^2)^{0.5}}$$

where "P" is the laser power; "Q" is the sensor quantum efficiency; "T" is the system transmission co-efficient, "n" is the water index of refraction; "A" is the entrance pupil area; $A_{pix}$ is the area of a pixel; "$E_{photon}$" is the energy of a photon; and "f" is the lens focal length.

4. The method in accordance with claim 3, said method further comprising the step of graphing the number of electrons within an image per pixel as a function of a focal plane position for attenuation coefficients.

5. The method in accordance with claim 4, said method further comprising the step of graphing a water range corresponding to a focal plane location and representing results of $$S = \frac{f(x_0^2 + f^2)^{0.5}}{(y_a - f)}$$

where S is a focal plane location.

\* \* \* \* \*